United States Patent
Abelgany

(10) Patent No.: US 8,652,178 B2
(45) Date of Patent: *Feb. 18, 2014

(54) POLYAXIAL PEDICLE SCREW ASSEMBLY AND METHOD

(75) Inventor: Mahmoud F. Abelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 578 days.

This patent is subject to a terminal disclaimer.

(21) Appl. No.: 12/909,811

(22) Filed: Oct. 21, 2010

(65) Prior Publication Data

US 2011/0034258 A1 Feb. 10, 2011

Related U.S. Application Data

(62) Division of application No. 11/045,908, filed on Jan. 28, 2005, now Pat. No. 7,862,594.

(60) Provisional application No. 60/548,543, filed on Feb. 27, 2004, provisional application No. 60/565,658, filed on Apr. 27, 2004.

(51) Int. Cl.
*A61B 17/88* (2006.01)

(52) U.S. Cl.
USPC .......................................... 606/279; 606/266

(58) Field of Classification Search
USPC .......................................... 606/60, 264–279
See application file for complete search history.

(56) References Cited

U.S. PATENT DOCUMENTS

| | | | |
|---|---|---|---|
| 3,054,321 A | 9/1962 | Macchia |
| 4,887,596 A | 12/1989 | Sherman |
| 4,946,458 A | 8/1990 | Harms et al. |
| 5,067,955 A | 11/1991 | Cotrel |
| 5,129,388 A | 7/1992 | Vignaud et al. |
| 5,246,442 A | 9/1993 | Ashman et al. |
| 5,360,431 A | 11/1994 | Puno et al. |
| 5,443,467 A | 8/1995 | Biedermann et al. |
| 5,466,237 A | 11/1995 | Byrd, III et al. |
| 5,474,555 A | 12/1995 | Puno et al. |
| 5,476,464 A | 12/1995 | Metz-Stavenhagen et al. |
| 5,520,689 A | 5/1996 | Schlapfer et al. |
| 5,536,268 A | 7/1996 | Griss |
| 5,545,165 A | 8/1996 | Biedermann et al. |
| 5,669,911 A | 9/1997 | Errico et al. |
| 5,672,176 A | 9/1997 | Biedermann et al. |

(Continued)

FOREIGN PATENT DOCUMENTS

| | | |
|---|---|---|
| DE | 19950075 | 4/2001 |
| EP | 1090595 A2 | 4/2001 |

(Continued)

*Primary Examiner* — Thomas J Sweet
*Assistant Examiner* — Michael Araj
(74) *Attorney, Agent, or Firm* — Rahman LLC

(57) ABSTRACT

A method comprising attaching a screw head to a bone fixator component, wherein the screw head comprises a first portion comprising a slot and an inwardly curved bottom portion; and a second portion comprising an outwardly protruding and expandable bulbous end extending from the inwardly curved bottom portion; and wherein the bone fixator component comprises a concave socket adapted to receive the screw head; securing the bone fixator component in a bone; securing a locking pin in the screw head; engaging the locking pin with the bone fixator component; inserting a longitudinal member in the screw head; and inserting a blocker in the screw head.

19 Claims, 16 Drawing Sheets

(56) References Cited

U.S. PATENT DOCUMENTS

| | | | |
|---|---|---|---|
| 5,733,286 | A | 3/1998 | Errico et al. |
| 5,735,851 | A | 4/1998 | Errico et al. |
| 5,752,957 | A | 5/1998 | Ralph et al. |
| 5,863,293 | A | 1/1999 | Richelsoph |
| 5,879,350 | A | 3/1999 | Sherman et al. |
| 5,882,350 | A | 3/1999 | Ralph et al. |
| 5,885,286 | A | 3/1999 | Sherman et al. |
| 5,951,553 | A | 9/1999 | Betz et al. |
| 5,964,760 | A | 10/1999 | Richelsoph |
| 5,964,767 | A | 10/1999 | Tapia et al. |
| 5,989,250 | A | 11/1999 | Wagner et al. |
| 6,022,350 | A | 2/2000 | Ganem |
| 6,030,389 | A | 2/2000 | Wagner et al. |
| 6,045,579 | A | 4/2000 | Hochshuler et al. |
| 6,053,917 | A | 4/2000 | Sherman et al. |
| 6,063,090 | A | 5/2000 | Schlapfer |
| 6,074,391 | A | 6/2000 | Metz-Stavenhagen et al. |
| 6,077,262 | A | 6/2000 | Schlapfer et al. |
| 6,090,110 | A | 7/2000 | Metz-Stavenhagen |
| 6,090,111 | A | 7/2000 | Nichols |
| 6,113,601 | A | 9/2000 | Tatar |
| 6,132,430 | A | 10/2000 | Wagner |
| 6,132,432 | A | 10/2000 | Richelsoph |
| 6,187,005 | B1 | 2/2001 | Brace et al. |
| 6,248,105 | B1 | 6/2001 | Schlapfer et al. |
| 6,273,888 | B1 | 8/2001 | Justis |
| 6,280,442 | B1 | 8/2001 | Barker et al. |
| 6,290,703 | B1 | 9/2001 | Ganem |
| 6,302,888 | B1 | 10/2001 | Mellinger et al. |
| RE37,665 | E | 4/2002 | Ralph et al. |
| 6,368,321 | B1 | 4/2002 | Jackson |
| 6,371,957 | B1 | 4/2002 | Amrein et al. |
| 6,416,515 | B1 | 7/2002 | Wagner |
| 6,454,769 | B2 | 9/2002 | Wagner et al. |
| 6,475,218 | B2 | 11/2002 | Gournay et al. |
| 6,485,491 | B1 | 11/2002 | Farris et al. |
| 6,485,492 | B1 | 11/2002 | Halm et al. |
| 6,488,681 | B2 | 12/2002 | Martin et al. |
| 6,554,834 | B1 | 4/2003 | Crozet et al. |
| 6,562,040 | B1 | 5/2003 | Wagner |
| 6,565,565 | B1 | 5/2003 | Yuan et al. |
| 6,595,992 | B1 | 7/2003 | Wagner et al. |
| 6,610,063 | B2 | 8/2003 | Kumar et al. |
| 6,613,050 | B1 | 9/2003 | Wagner et al. |
| 6,623,485 | B2 | 9/2003 | Doubler et al. |
| 6,626,908 | B2 | 9/2003 | Cooper et al. |
| 6,641,586 | B2 | 11/2003 | Varieur |
| 6,648,888 | B1 | 11/2003 | Shluzas |
| 6,660,004 | B2 | 12/2003 | Barker et al. |
| 6,736,820 | B2 | 5/2004 | Biedermann et al. |
| 6,780,186 | B2 | 8/2004 | Errico et al. |
| 6,858,030 | B2 | 2/2005 | Martin et al. |
| 6,890,334 | B2 | 5/2005 | Brace et al. |
| 6,974,460 | B2 | 12/2005 | Carbone et al. |
| 7,022,122 | B2 | 4/2006 | Amrein et al. |
| RE39,089 | E | 5/2006 | Ralph et al. |
| 7,118,571 | B2 | 10/2006 | Kumar et al. |
| 7,128,743 | B2 | 10/2006 | Metz-Stavenhagen |
| 7,163,539 | B2 * | 1/2007 | Abdelgany et al. .......... 606/86 A |
| 7,335,201 | B2 | 2/2008 | Doubler et al. |
| 7,524,326 | B2 | 4/2009 | Dierks |
| 2002/0010467 | A1 | 1/2002 | Cooper et al. |
| 2003/0055426 | A1 | 3/2003 | Carbone et al. |
| 2003/0073996 | A1 | 4/2003 | Doubler et al. |
| 2003/0163133 | A1 | 8/2003 | Altarac et al. |
| 2003/0199873 | A1 | 10/2003 | Richelsoph |
| 2004/0153077 | A1 | 8/2004 | Biedermann et al. |

FOREIGN PATENT DOCUMENTS

| | | |
|---|---|---|
| EP | 1254640 A2 | 11/2002 |
| EP | 1293168 A2 | 3/2003 |
| WO | WO9834554 | 8/1998 |
| WO | WO9955246 A1 | 11/1999 |
| WO | WO0122893 A1 | 4/2001 |
| WO | WO03068088 A1 | 8/2003 |

* cited by examiner

Section C-C

Detail A

Section A-A

Section B-B

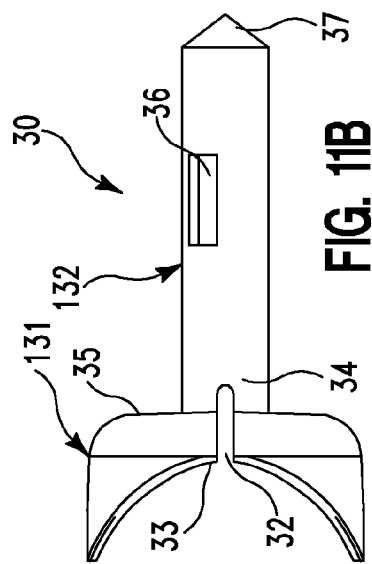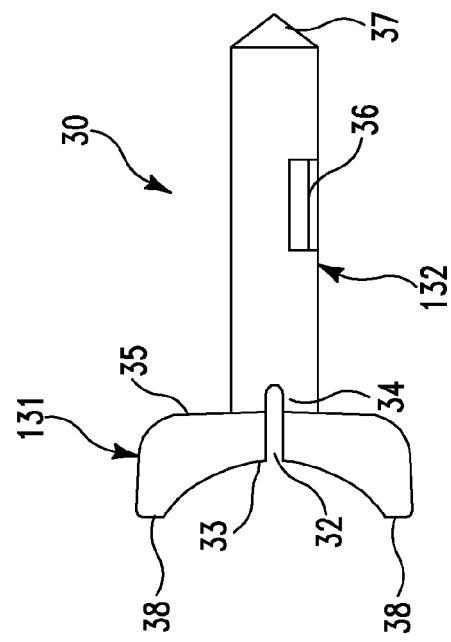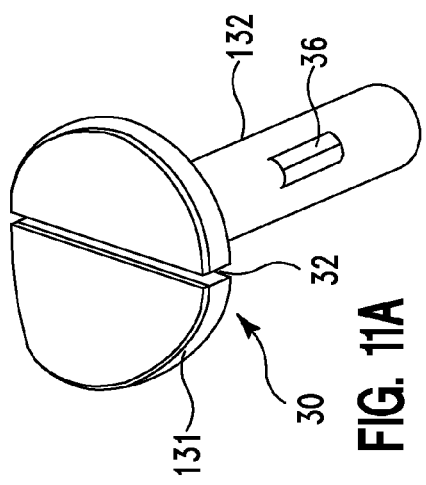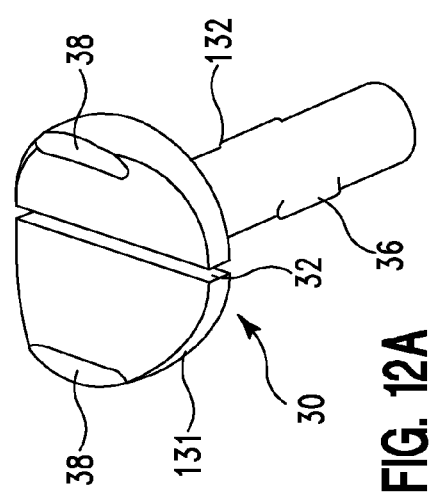

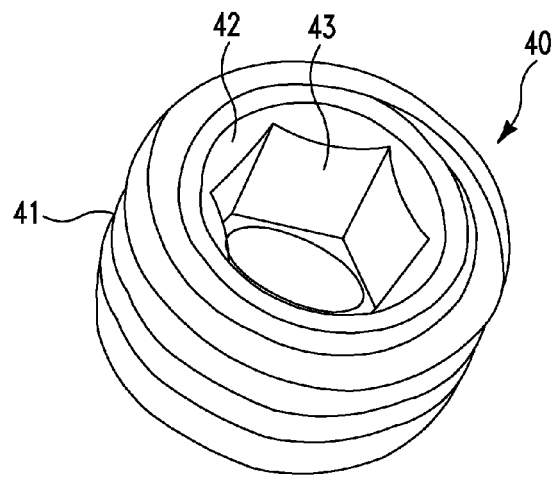
FIG. 15A
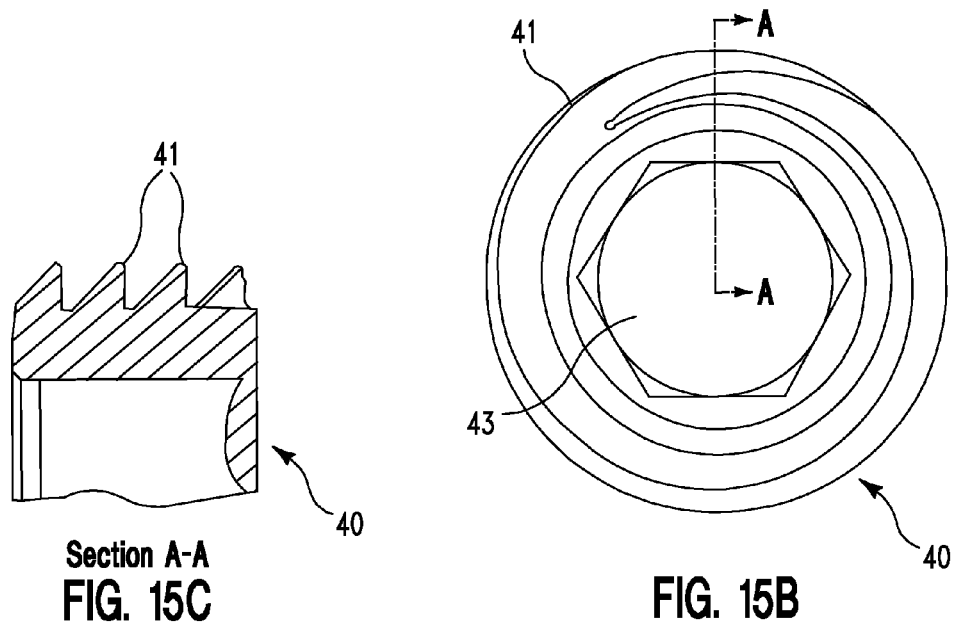
Section A-A
FIG. 15C
FIG. 15B

POLYAXIAL PEDICLE SCREW ASSEMBLY AND METHOD

CROSS REFERENCE TO RELATED APPLICATION

This application is a divisional patent application of U.S. utility patent application Ser. No. 11/045,908 filed Jan. 28, 2005, which claims the benefit of U.S. Provisional Patent Application No. 60/548,543 filed on Feb. 27, 2004 and U.S. Provisional Patent Application No. 60/565,658 filed on Apr. 27, 2004, whereby the contents of all three applications, in their entireties, are herein incorporated by reference.

BACKGROUND

1. Technical Field

The embodiments herein generally relate to medical devices and assemblies, and more particularly to an orthopedic surgical implant assembly used in the field of surgical lumbar, thoracic and cervical spine treatment.

2. Description of the Related Art

Surgical procedures treating spinal injuries are one of the most complex and challenging surgeries for both the patient and the surgeon. When there are various deformities, trauma, or fractures of the vertebra, surgeons may attempt to "fuse" them together by attaching screw-like devices into the pedicles of the spine and thereby connecting several vertebrae (typically two or more) using a semi-rigid rod. However, due to the complexity of the human anatomy, most surgeons must bend the rod (causing notches thereby reducing fatigue resistance) before placing them into two or more non-aligned pedicle screws in order to properly stabilize the pedicle screw assembly within the patient's body.

Depending on the purpose of the spine surgery, indications, and patient size, surgeons must pre-operatively choose between different spinal systems with differing rod sizes pre-operatively sometimes causing delays in surgery while waiting for more adequate systems to be sterilized. Some surgeons prefer monoaxial screws for rigidity, while some sacrifice rigidity for surgical flexibility in screw placement. Therefore, a system is needed to accommodate both theories. For example, during scoliosis surgery conventional polyaxial systems typically cannot lock into a desired position to persuade the spinal column into desired correction before final construct assembly.

Most conventional top loading polyaxial spine screws do not do enough to address cantilever failure of the assembly components. Additionally, most polyaxial screws generally do not offer enough flexibility because the rod sits too closely on top of the center of rotation. Furthermore, most top loading screw systems generally do not accommodate different rod sizes. Thus, there remains a need for a new and improved pedicle screw assembly capable of overcoming the limitations of the conventional designs thereby providing the surgeon with improved intra-operative flexibility and the patient with an improved prognosis for better and complete rehabilitation.

SUMMARY

In view of the foregoing, an embodiment herein provides a method comprising attaching a screw head to a bone fixator component, wherein the screw head comprises a first portion comprising a slot and an inwardly curved bottom portion; and a second portion comprising an outwardly protruding and expandable bulbous end extending from the inwardly curved bottom portion; and wherein the bone fixator component comprises a concave socket adapted to receive the screw head; securing the bone fixator component in a bone; securing a locking pin in the screw head; engaging the locking pin with the bone fixator component; inserting a longitudinal member in the screw head; and inserting a blocker in the screw head.

The method may further comprise coating the screw head and the bone fixator component with a wear resistant ceramic coating. The method may further comprise configuring said bone fixator component as a bone screw. Alternatively, the method may further comprise configuring said bone fixator component as a hook.

Another embodiment provides a method of assembling a pedicle fixation assembly, wherein the method comprises attaching a screw head to a bone fixator component; securing the bone fixator component in a bone; securing a locking pin in the screw head; engaging the locking pin with the bone fixator component; inserting a longitudinal member in the screw head; and inserting a blocker in the screw head. The screw head may comprise a male bulbous end and the bone fixator component may comprise a female concave semi-spherical socket for receiving the screw head. The method may further comprise coating the screw head and the bone fixator component with a wear resistant ceramic coating. The method may further comprise configuring the bone fixator component as a bone screw. Alternatively, the method may further comprise configuring the bone fixator component as a hook.

Another embodiment provides a method of using a pedicle screw assembly, the method comprising providing a screw head comprising a first portion comprising a slot and a curved bottom portion; and a second portion comprising an outwardly protruding and expandable bulbous end extending from the curved bottom portion; providing a bone fixator component comprising a concave socket that receives the screw head, wherein the bone fixator component is located completely outside of the screw head; providing a locking pin that is adapted to be inserted through the screw head causing expansion of the expandable bulbous end of the screw head; and providing a blocker that is adapted to engage the screw head. The method may further comprise providing the screw head and the bone fixator component with a wear resistant ceramic coating. The method may further comprise configuring the bone fixator component as a bone screw. Alternatively, the method may further comprise configuring the bone fixator component as a hook.

Another embodiment provides a method comprising providing a screw head comprising a slot and a bottom portion; providing a polyaxial rotatable connecting end operatively connected to the bottom portion of the screw head; providing a bone fixator component comprising a concave socket that receives the polyaxial rotatable connecting end; configuring the rotatable connecting end to engage the bone fixator component; and providing a blocker that engages the screw head. A combination of the bottom portion of the screw head with the polyaxial rotatable connecting end may form a substantially bulbous body. In one embodiment, the bone fixator component is located completely outside of the screw head. The bottom portion of the screw head and the polyaxial rotatable connecting end may be adapted to be locked into the concave socket of the bone fixator component. The method may further comprise providing the screw head and the bone fixator component with a wear resistant ceramic coating. The method may further comprise configuring the bone fixator component as a bone screw. Alternatively, the method may further comprise configuring the bone fixator component as a hook.

The embodiments herein provide a pedicle screw assembly implant device, which may be used anteriorly or posteriorly, and which is capable of being utilized in surgeries to achieve anterior lumbar interbody fusion, posterior lumbar interbody fusion, transverse lumbar interbody fusion, correct degenerative disc disease, adult and pediatric scoliosis as a fixation device, and posterior cervical fusion.

The embodiments herein provide a polyaxial spinal screw that can become rigid similar to a monoaxial screw interoperatively on demand. The embodiments herein also offer the surgeon more lateral range of motion than conventional products by utilizing the space under the screw head to provide a bigger arc of rotation. Moreover, the saddle pin component offers the flexibility to use a diametrical range of spinal rods instead of a fixed size rod.

These and other aspects of the embodiments herein will be better appreciated and understood when considered in conjunction with the following description and the accompanying drawings. It should be understood, however, that the following descriptions, while indicating preferred embodiments herein and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 11A through 11B are detailed views of the saddle pin according to a first embodiment herein;

FIGS. 12A through 12B are detailed views of the saddle pin according to a second embodiment herein;

FIGS. 15A through 15C are detailed views of the blocker according to an embodiment herein.

DETAILED DESCRIPTION OF PREFERRED EMBODIMENTS HEREIN

Figure 1:
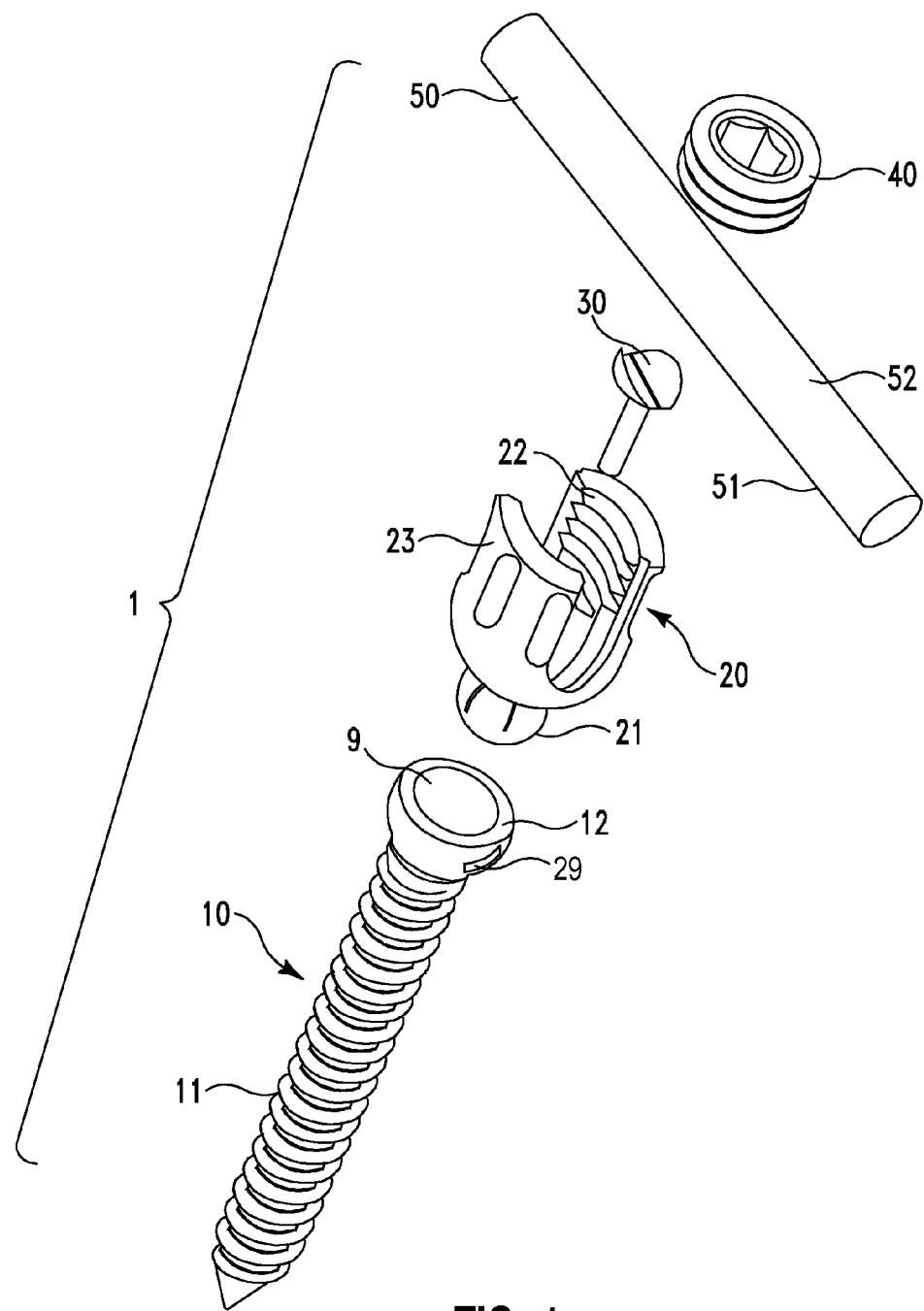
FIG. 1 illustrates an exploded view of the screw assembly according to an embodiment herein.

The embodiments herein and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new and improved pedicle screw assembly capable of overcoming the limitations of the conventional designs thereby providing the surgeon with improved intra-operative flexibility and the patient with an improved prognosis for better and complete rehabilitation. The embodiments herein address this need by providing an improved polyaxial pedicle screw device and method of assembly capable of accommodating multiple rod diameters and withstanding higher failure strengths. Referring now to the drawings and more particularly to FIGS. 1 through 16 where similar reference characters denote corresponding features consistently throughout the figures, there are shown preferred embodiments herein.

FIGS. 1 through 6 provide an exploded view of the pedicle screw assembly 1 according to a first embodiment herein. The screw assembly 1 comprises a bone screw (fixator component) 10 having a threaded end 11 for engaging a bone (not shown) and a concave female socket end 12 for engaging and receiving the screw head 20.

Figure 2:
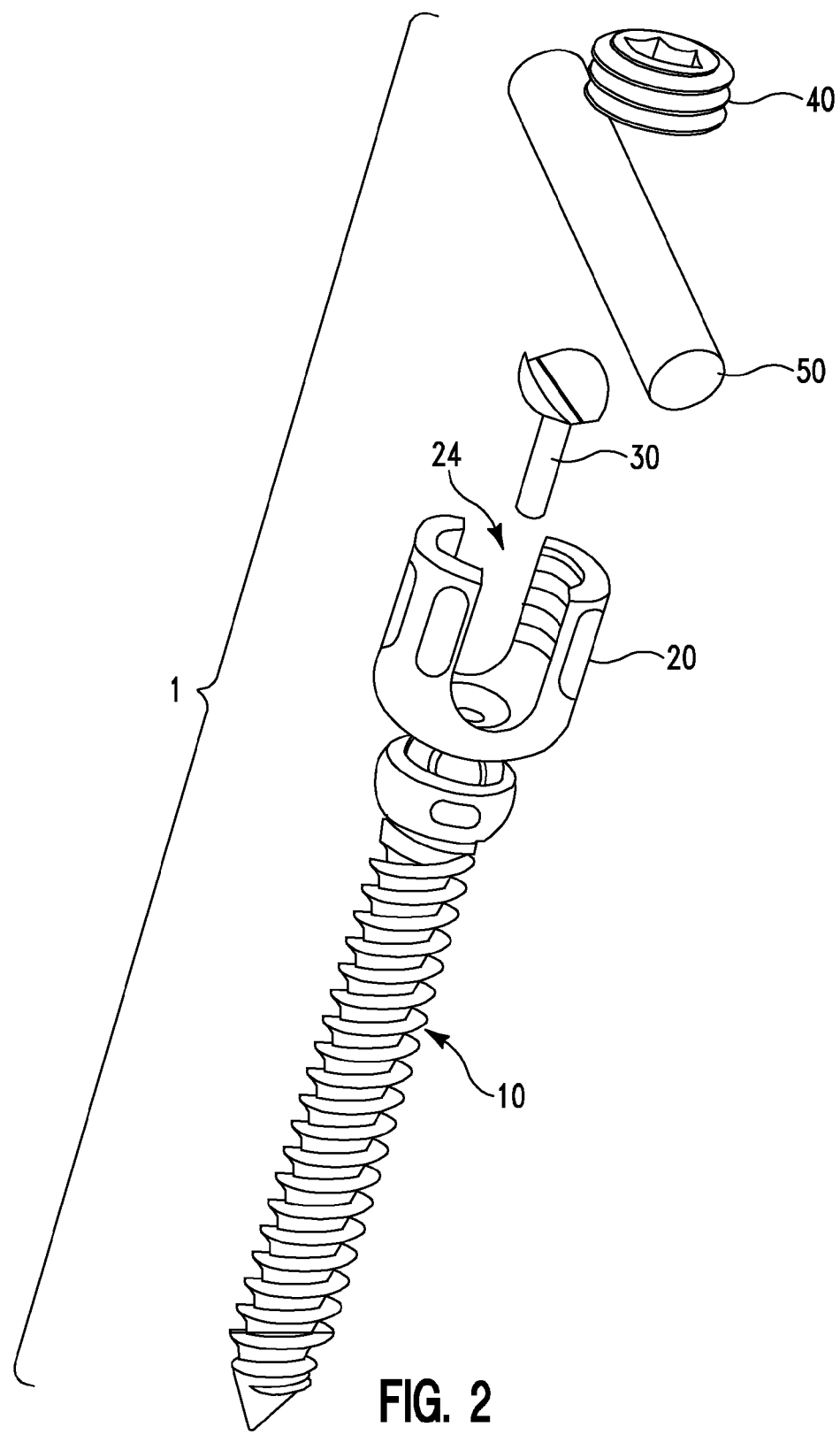
FIG. 2 illustrates an exploded view of the screw assembly during a step in the manufacturing according to an embodiment herein.
Figure 3:
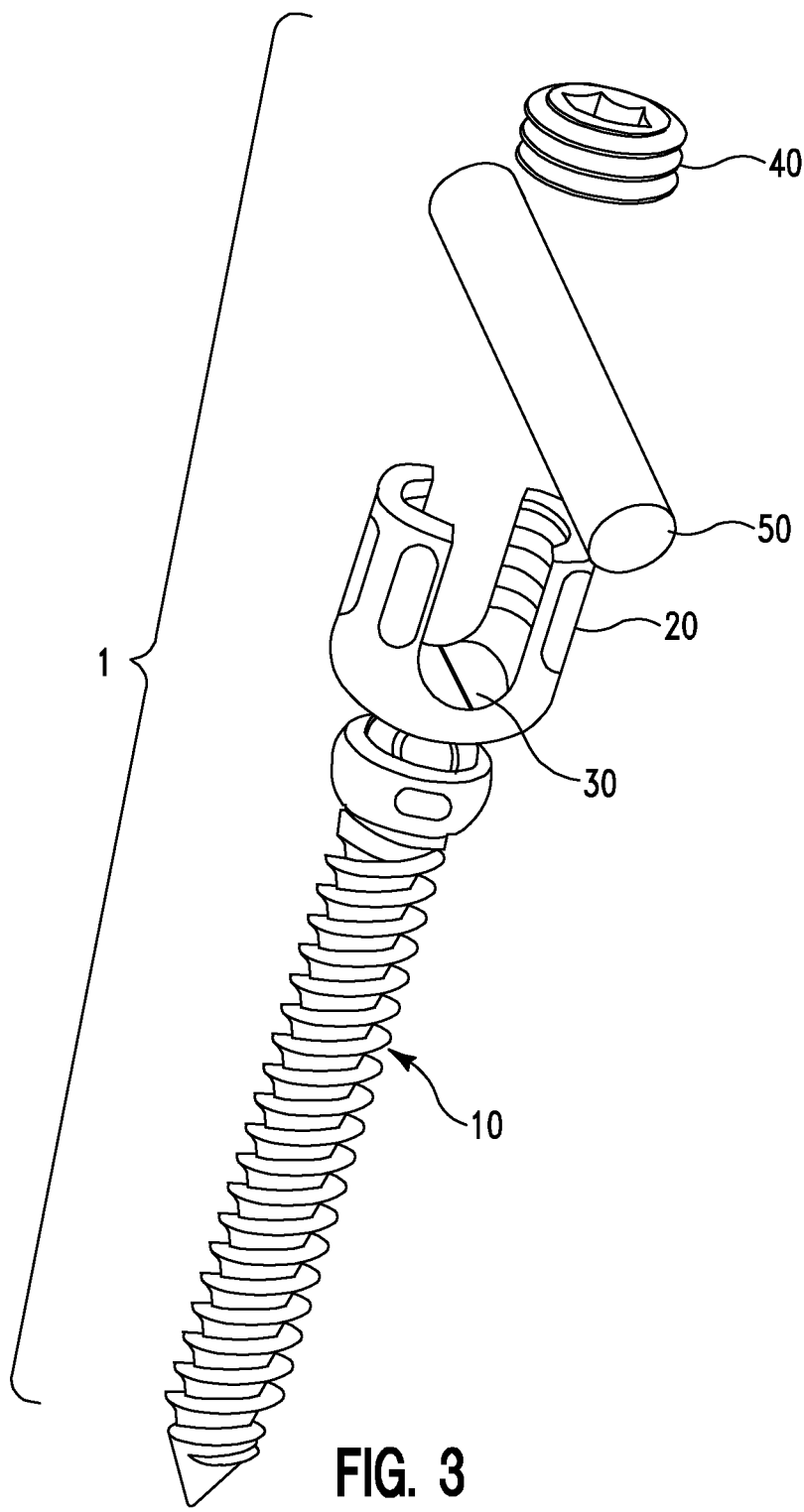
FIG. 3 illustrates an exploded view of the screw assembly during a step in the manufacturing according to an embodiment herein.

As implemented, the screw head 20 is first snapped into place in the bone screw 10 as shown in FIG. 2. Then, as shown in FIGS. 3 and 9B, the saddle pin 30 snaps into place in the lower base portion 25 of the screw head 20, which includes a groove 26 (best seen in FIG. 7) for receiving the saddle pin 30. In the manufacturing process, once the saddle pin 30 snaps into place, the screw assembly 1 is prepared for ultra sonic cleaning to remove any impurities and subsequently may be shipped in this manufactured format (with the saddle pin 30 connected to the screw head 20, which is connected to the bone screw 10).

Figure 7:
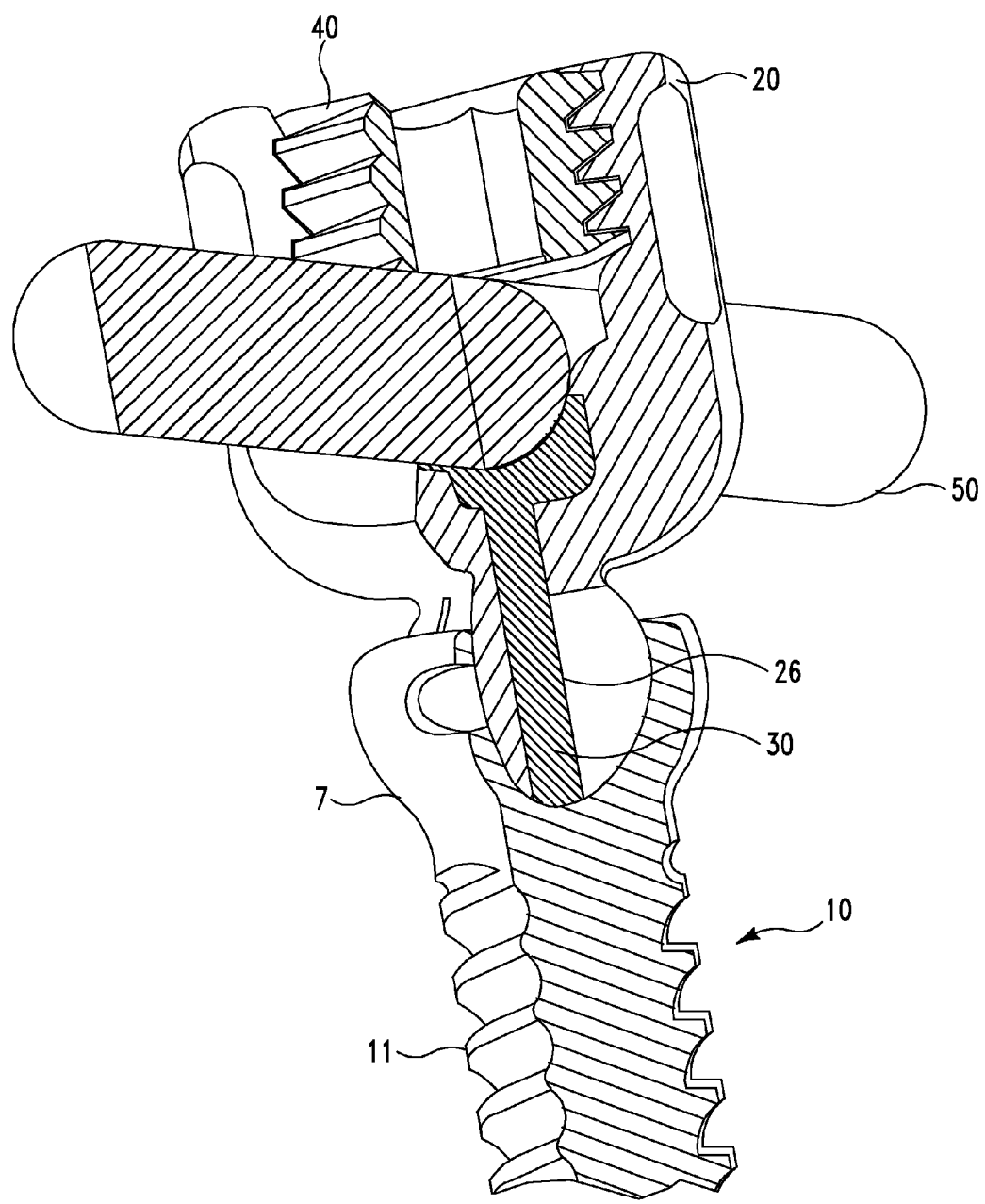
FIG. 7 is a partial internal view of the screw assembly in a monoaxial position according to an embodiment herein.
Figure 8:
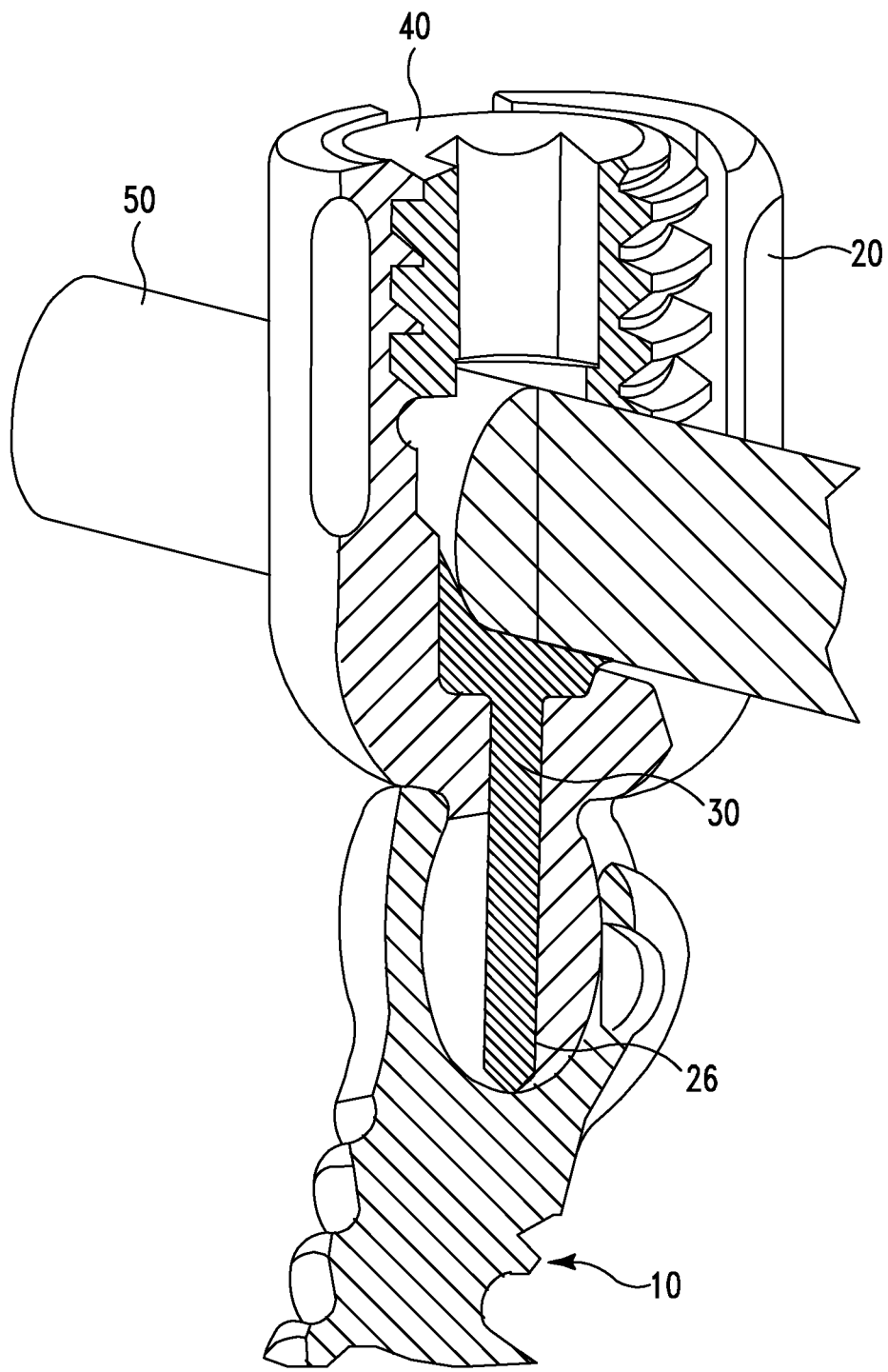
FIG. 8 is a partial internal view of the screw assembly in a polyaxial position according to an embodiment herein.

FIG. 7 shows that the female spherical socket 12 of the bone screw 10 has an undercut 7 to allow the screw head 20 to pivot freely but not to disassemble once the saddle pin 30 is inserted. The thread 11 of the bone screw 10 may be a multiple lead thread to allow faster insertion into a bone. This thread 11 may be tapered on the minor diameter while cylindrical on the major diameter to allow a new "bite" with every turn and to accommodate more thread depth towards the bottom of the bone screw 10 for the cancellous bone.

Figure 4:
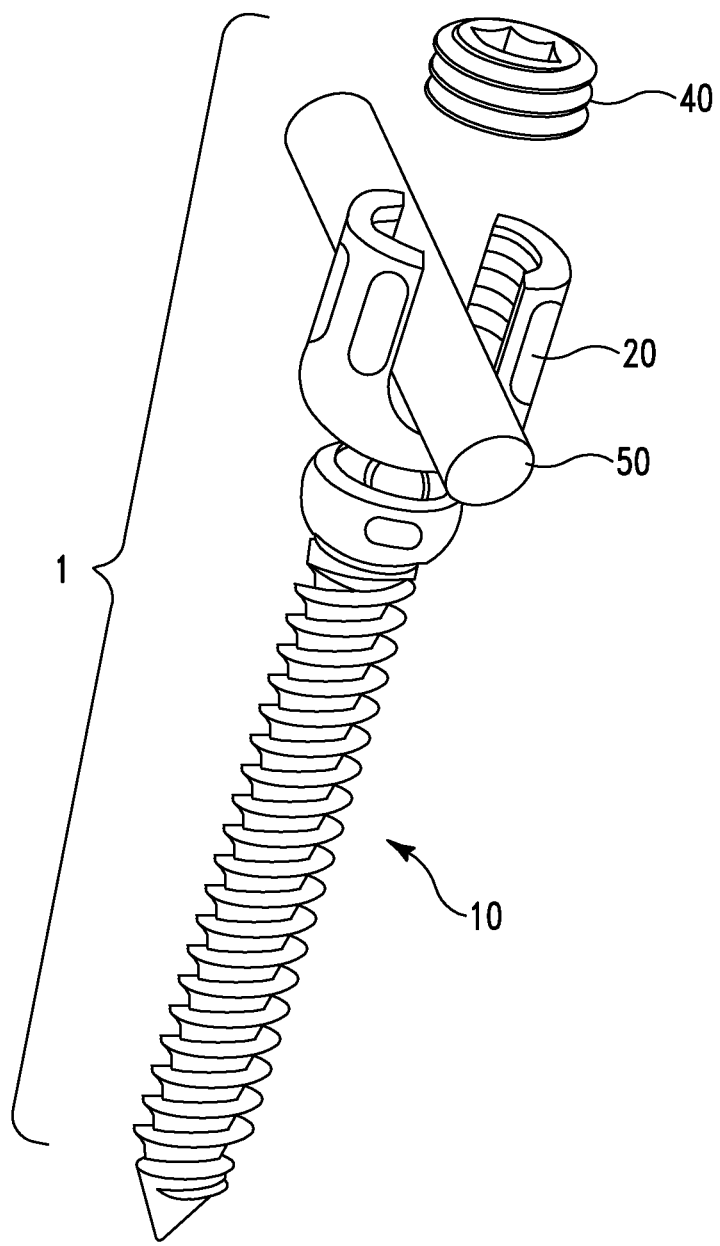
FIG. 4 illustrates an exploded view of the screw assembly during a step in the manufacturing according to an embodiment herein.
Figure 5:
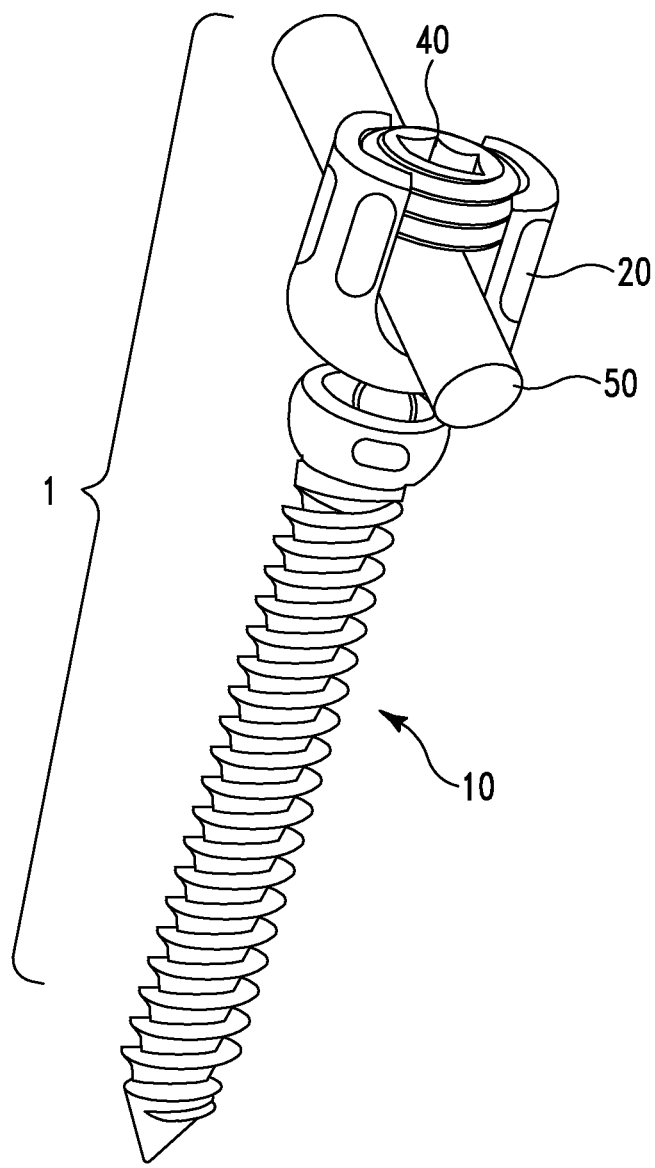
FIG. 5 illustrates a perspective view of the fully assembled screw assembly in a monoaxial position according to an embodiment herein.
Figure 6:
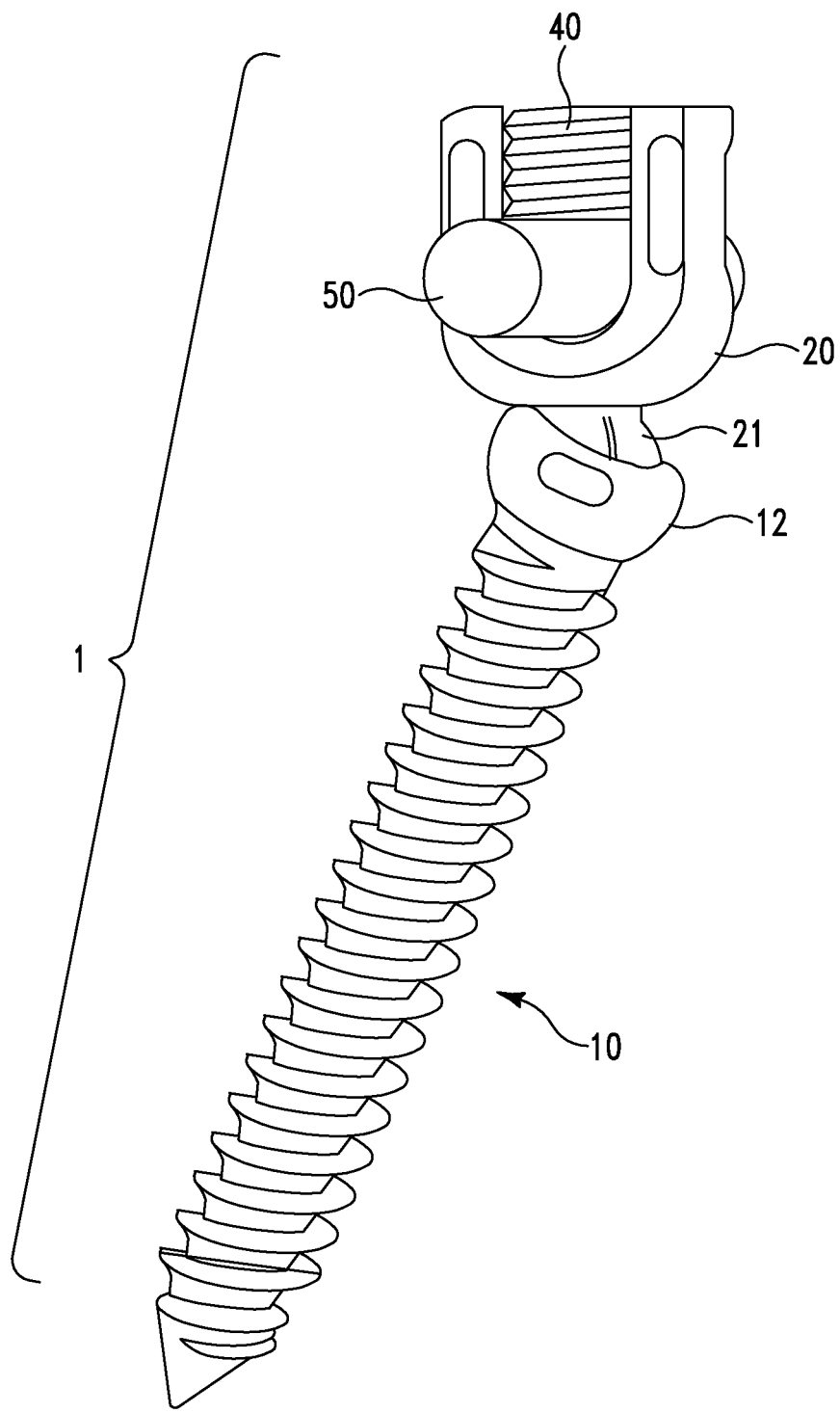
FIG. 6 illustrates a perspective view of the fully assembled screw assembly in a polyaxial position according to an embodiment herein.

Once the bone screw 10 is inserted into the bone, a longitudinal member 50, which may be embodied as a rod, bar, etc. and blocker 40 are inserted into the screw assembly 1, as illustrated in FIG. 4. The screw head 20 can accommodate 5.5 mm as well as 6.0 mm rods, which is advantageous over conventional screw assemblies that are limited to accepting only rods of a uniform dimension. FIG. 5 illustrates the assembled view of the screw assembly 1 in the straight monoaxial direction. The threads 11 of the bone screw 10 are double lead, which provides greater surface contact with the bone, but drives at 4 mm/revolution. FIG. 6 illustrates the screw assembly 1 in a rotationally articulated position. The maximum angulation is 25 degrees/side, but the medial correction/travel of the longitudinal member 50 is 3.8 mm/side, which is nearly twice of what most conventional screws offer.

In FIG. 7, the locking mechanism of the screw assembly 1 is illustrated. Here, a two-step locking process is shown. The first position expands the screw head 20 into the bone screw 10, and the second position permanently turns the polyaxial screw assembly 1 into a monoaxial screw assembly 1 by using the saddle pin 30 to lock the assembly 1. As FIG. 8 demonstrates, the screw assembly 1 can be permanently locked in any desired position (within the 25 degree guideline) simply by sending the longitudinal member 50 "home" or by using a tool (not shown) to lock the assembly 1 at the desired angle.

Figure 9A:
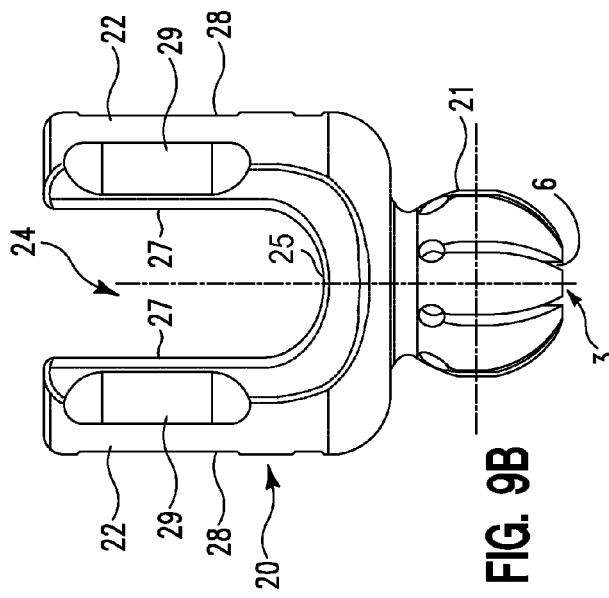
FIGS. 9A through 9H are isolated views of the screw head according to an embodiment herein.
Figure 9B:
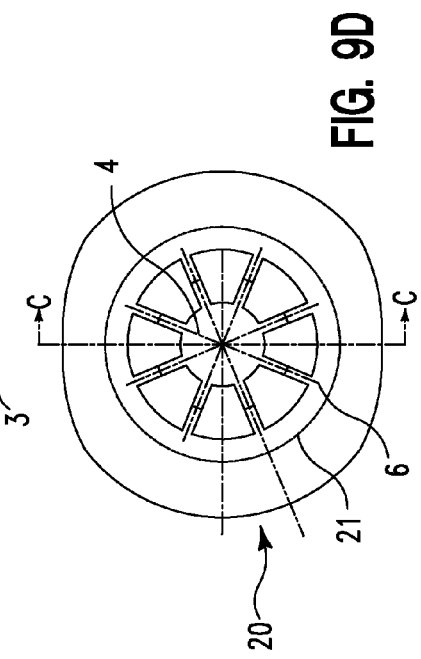
Figure 9C:
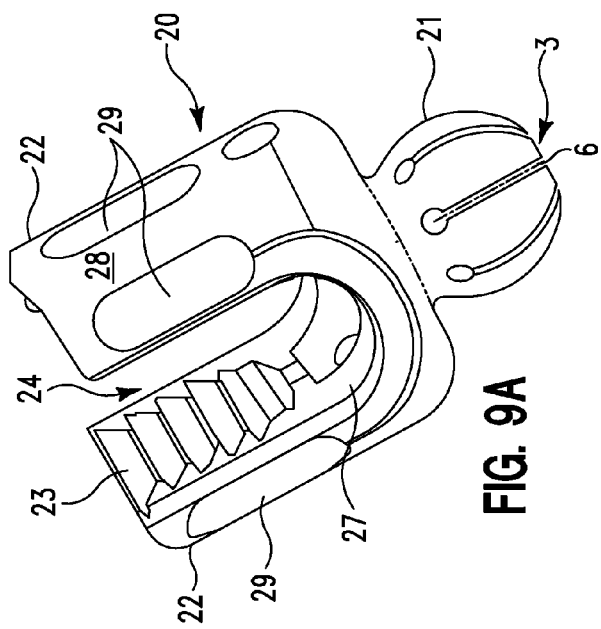
Figure 9D:
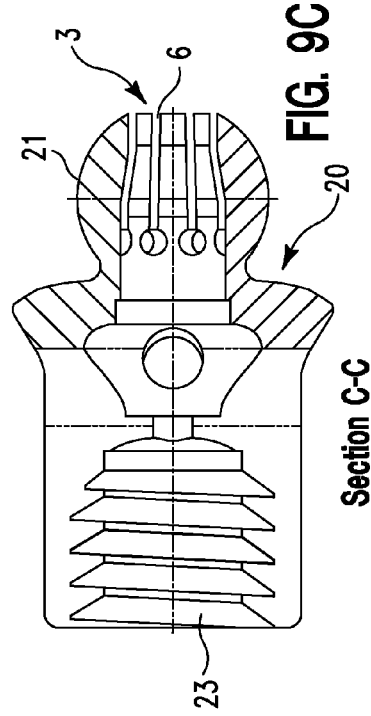
Figure 9H:
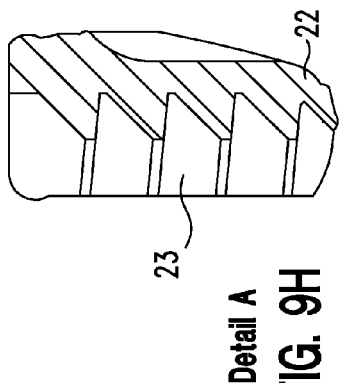
Figure 9G:
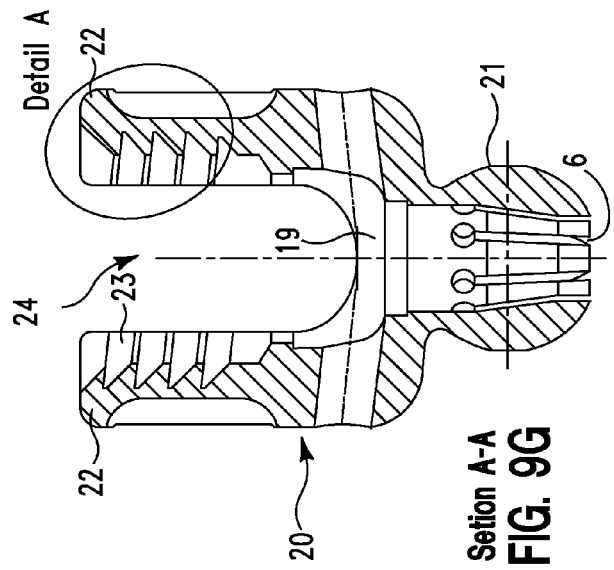
Figure 9E:
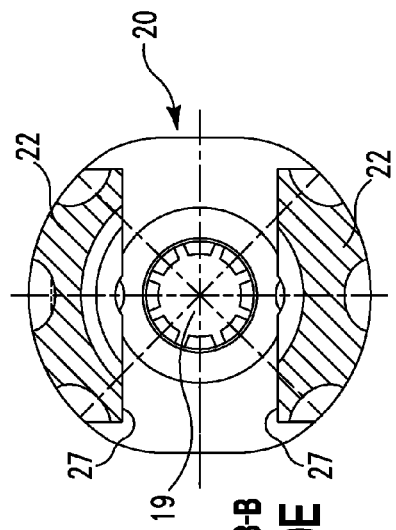
Figure 9F:
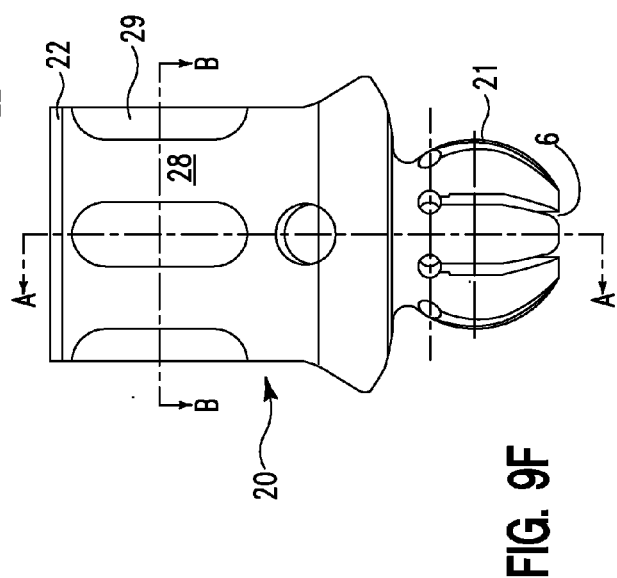

FIG. 9A illustrates the overall configuration of the screw head 20. FIG. 9B illustrates a front view of the screw head 20. FIG. 9C is a cross-sectional view from cut-line "CC" of FIG. 9D. FIG. 9E is a cross-sectional view from cut-line "BB" of FIG. 9F and FIG. 9G is a cross-sectional view from cut-line "AA" of FIG. 9F. Additionally, FIG. 9H is an enlarged detailed view of the encircled area "A" of FIG. 9G illustrating the threaded inner portion 23 in more detail. As shown in FIGS. 9A through 9H, the screw head 20 includes a bulbous (spherical) male end 21 for engaging the concave female socket 12 of the bone screw 10. The screw head 20 also includes a pair of upright ends 22 opposite the bulbous male end 21, wherein the upright ends 22 comprise a threaded inner portion 23 for engaging the blocker 40. Furthermore, the screw head 20 includes a generally open U-shaped inner portion 24 for receiving the saddle pin 30 and the longitudinal member 50. The male end 21 of the screw head 20 includes a plurality (for example, four or more) slots 6 that allow the male end 21 to expand into the female spherical socket 12 of the bone screw 10 at any allowable angle once the saddle pin 30 is forced through.

Since the screw head 20 is pivoting inside the female socket end 12 of the bone screw 10, the assembly 1 is allowed to be inserted deeper into the bone without having the bone or anatomy prematurely limit the range of angulations of the screw head 20. The screw head 20 further includes external features or cuts 29 that assist in accommodating surgical instrumentation during manipulation and assembly during the surgical procedure. These cuts 29 allow various instruments (not shown) to firmly and positively hold and manipulate the screw head 20 on one side or both sides of screw head 20.

Figure 10A:
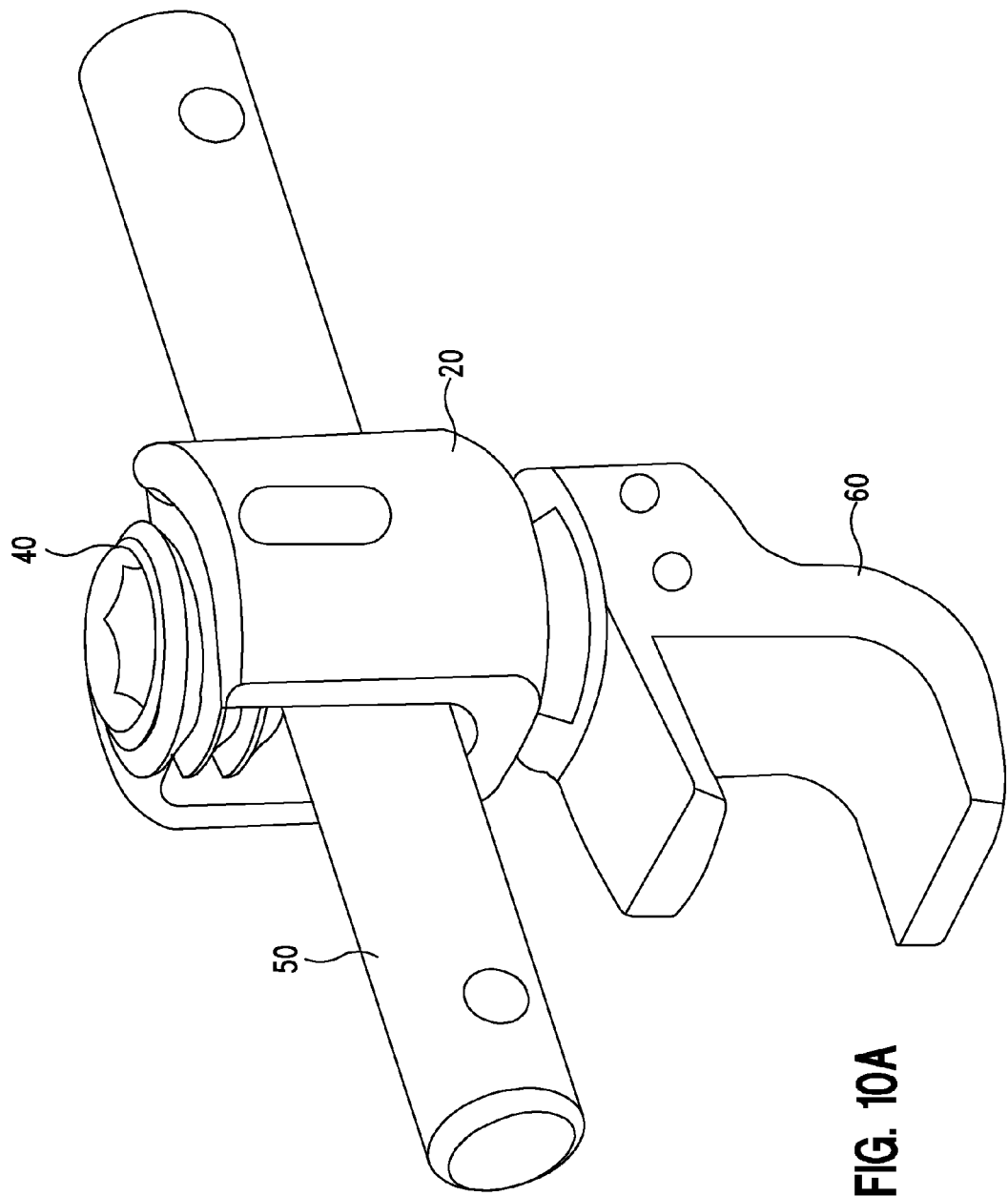
FIG. 10A is a perspective view of a bone fixator assembly according to a second embodiment herein.

FIG. 10A is a perspective view of a bone fixator assembly according to a second embodiment herein, wherein the bone fixator component is configured as a hook 60. The hook 60 is further illustrated in FIG. 10B. The hook 60 includes a concave socket 12 having an inner portion 9 adapted to receive the bulbous end 21 of the screw head 20; and a dimpled outer portion 8. The hook 60 further includes a pair of arms 61, 62 connected by a connection arm 64. A space 63 separates the arms 61, 62 from one another. The arms 61, 62 are configured to receive an additional member (not shown) for subsequent attachment to the bone.

The several embodiments of the saddle pin 30 are shown in FIGS. 11A through 14. The saddle pin 30 provides a proper seat for the longitudinal member 50 and avoids notching a typical titanium longitudinal member 50 (titanium is very notch sensitive). Furthermore, the saddle pin 30 allows one to accommodate multiple sizes of longitudinal members 50 in the same screw assembly system 1 which is a first for a titanium system because of the above-mentioned notching factors. The saddle pin 30 is configured with a slot 32 through the center to allow expansion of the upper portion (head) 131 of the saddle pin 30. The bottom 35 of the saddle pin head 131 is angled to allow the saddle pin 30 to accept a larger-sized longitudinal member 50. The saddle pin 30 initially expands the male sphere 21 of the screw head 20 into the female spherical socket 12 in the bone screw 10 causing the screw assembly system 1 to lock or start locking (i.e., causing the male sphere 21 of the screw head 20 to lock in the female spherical socket 12 of the bone screw 10). The saddle pin 30 then "digs" into the female spherical socket 12 of the bone screw 10 to provide a secondary locking force to avoid bending failure of the assembly 1.

FIGS. 11A through 11B illustrate a first embodiment of the saddle pin 30. The saddle pin 30 generally includes an upper portion 131 and a lower portion 132. The upper portion includes a slot 32, which is configured from the lowest area 33 of the upper portion 131 into the upper area 34 of the lower portion 132 of the saddle pin 30. A secondary locking mechanism 36 may be configured on the lower portion 132 of the saddle pin to further achieve locking of the saddle pin 30 once it is inserted in the screw head 20. The lower portion 132 of the saddle pin 30 terminates with a pointed end 37 to allow for digging into the female socket 12 of the bone screw 10. FIGS. 12A through 12B illustrate a second embodiment of the saddle pin 30. The difference between the first and second embodiments of the saddle pin 30 is that the upper portion of the saddle pin 131 in the second embodiment includes two generally flat upper opposed ends 38 to more matingly configure with the geometry of the screw head 20 and the longitudinal member 50.

Figure 14:
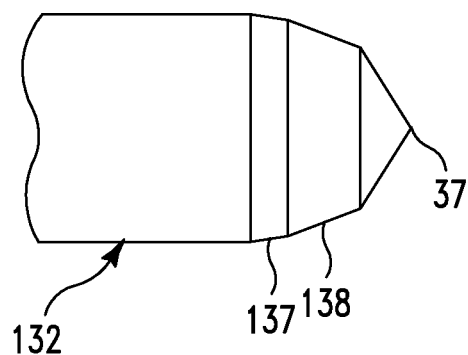
FIGS. 13 through 14 are detailed views of the saddle pin according to a third embodiment herein.
Figure 13:
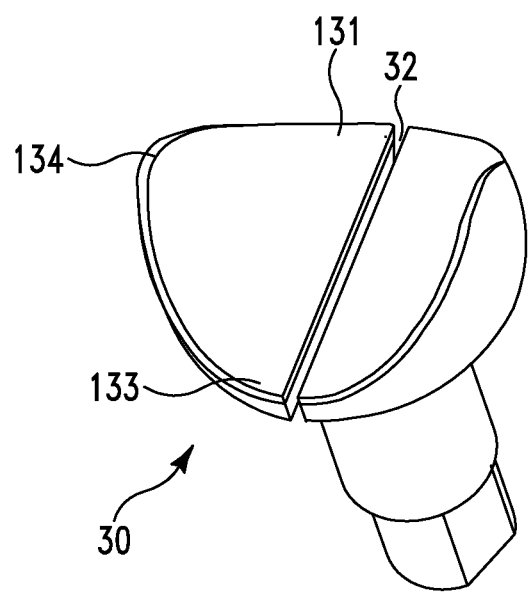

FIGS. 13 through 14 illustrate a third embodiment of the saddle pin 30. In particular, in the third embodiment, the saddle pin 30 comprises two parts: an upper portion 131 preferably comprising titanium and a lower portion 132 which is preferably ceramic. According to the third embodiment, the material of the lower portion 132 of the saddle pin 30 is preferably ceramic and has a higher hardness and compressive yield strength than the comparative hardness and compressive yield strength of $Ti_6Al_4V$, which is the material which may be used in constructing the screw head 20 and bone screw 10.

As shown in FIG. 13, the upper portion 131 of the saddle pin 30 includes a slot 32 in the seat portion 133 and tapered angled ends 134. Preferably, the saddle pin 30; i.e., the upper portion 131 and the ceramic tip 132 are assembled last in the overall process. Specifically, the screw head 20 snaps into the bone screw 10. Then, the ceramic tip 132 slides into the screw head 20, and finally the titanium saddle (upper portion) 131 is press fitted into the screw head 20 keeping everything in place and oriented in a relaxed state.

As best seen in FIG. 14, the lower portion 132 of the saddle pin terminates with a series of cascading walls 137, 138 having sloped angles, terminating with the pointed end 37 for attachment into the screw head 20/bone screw 10 assembly. The material properties of the saddle pin tip 132 are such that it prevents the deformation on the saddle pin 30 before the saddle pin 30 gives the proper bending and penetrating effects onto the screw head 20/bone screw 10 assembly. Examples of the types of materials used for the saddle pin pointed end 37 include Zyranox™ and HIP Vitox™, both of which are available from Morgan Advanced Ceramics, United Kingdom.

The blocker 40, which is further illustrated in FIGS. 15A through 15C, includes a standard buttress thread 41 configured along an outer perimeter of the blocker 40. The blocker 40 helps to secure the longitudinal member 50 inside the screw head 40. The threads 41 of the blocker 40 are configured to engage the threads 23 of the screw head 20. Additionally, the blocker 40 aids in preventing the expansion of the screw head 20 when torqued on the longitudinal member 50, directing the counterforce more vertically than horizontally. The top 42 of the blocker 40 has a fastening feature 43 such as a hex or square lock feature to allow high torque to be applied in locking the assembly 1. Furthermore, the blocker 40 may be configured with a free rotating saddle (not shown) to accommodate, via tangential contact, the longitudinal member 50 and help to further prevent notching of the titanium alloy used to construct the longitudinal member 50. Moreover, the blocker 40 may have a "timed" thread 41 that is consistently and precisely related to the blocker driving tool (not shown) to help calculate the torsional and vertical position of the blocker 40 thereby assisting the torque measurement applied to the blocker 40.

Figure 16:
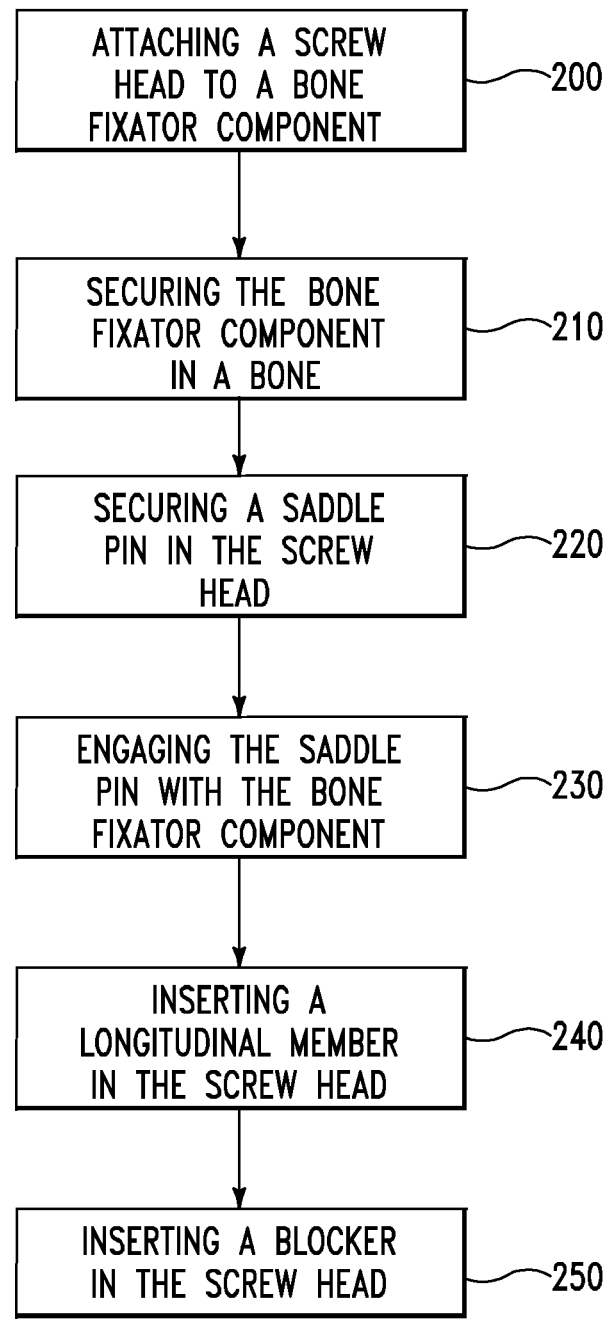
FIG. 16 is a flow diagram illustrating a preferred method according to an embodiment herein.

Another aspect of the embodiments herein is illustrated in the flowchart of FIG. 16, which includes descriptions which refer to components provided in FIGS. 1 through 15C. FIG. 16 illustrates a method of assembling a pedicle screw assembly 1, wherein the method comprises attaching (200) a screw head 20 to a bone fixator component 10, 60; securing (210) the bone fixator component 10, 60 in (or operatively connected to) the bone (not shown); securing (220) a saddle pin 30 in the screw head 20; engaging (230) the saddle pin 30 with the bone fixator component 10, 60; inserting (240) a longitudinal member 50 in the screw head 20; and inserting (250) a blocker 40 in the screw head 20. As mentioned, the embodiments herein provide an axial movement of the screw head up to 25 degrees in any plane. Moreover, the embodiments herein allow for greater medial translation of the longitudinal member 50 (nearly 4 mm compared to the conventional devices which are generally limited to 2 mm).

Moreover, according to an aspect of the embodiments herein, the inventive assembly 1 can be used as a dynamic rod system to complement artificial discs. According to this embodiment, the outside of the spherical joint part 21 of the screw head 20 and the inner spherical surface 9 of the bone screw cup 12 are coated with a wear resistant ceramic coating. In this scenario, the saddle pin 30 is not digging into the bone screw 10 and in fact is configured at a shorter length than some of the other embodiments. This system allows some motion instead of rigid fixation and shares the load with the artificial disc disallowing excessive forces being applied to the artificial disc and increasing its functional life. For example, this occurs as a result of the ceramic coating, which may be used in the embodiments herein. As such, the spherical joint 21 of the screw head 20 and the inner spherical surface 12 of the bone screw 10 have lower friction and higher wear resistance characteristics, thus improving the overall characteristics of the screw assembly 1.

Generally, as shown in FIGS. 1 through 15C, the embodiments herein provide an assembly 1 comprising a screw head 20 comprising a bulbous end 21; a fixator component 10 configured for receiving the bulbous end 21 of the screw head 20; a pin 30 mounted in the screw head 20; and a blocker 40 adapted to engage the screw head 20. The screw head 20 comprises a slot 24 configured for receiving a longitudinal member 50. The fixator component 10 comprises a concave socket 12 configured for receiving the bulbous end 21 of the screw head 20. In a first embodiment, the fixator component 10 also comprises a threaded end 11 opposite the concave socket 12 and configured for attaching to a bone. The pin 30 engages the fixator component 10 and a bottom portion 51 of the longitudinal member 50. The blocker 40 secures a top portion 52 of the longitudinal member 50. The pin 30 comprises an upper saddle portion 131 and a lower tip portion 132.

Additionally, the pin 30 may comprise a multi-part assembly. The upper saddle portion 131 of the pin 30 comprises titanium and the lower tip portion 132 of the pin 30 comprises a ceramic material. Moreover, the lower tip portion 132 comprises a mechanically harder material than the upper saddle portion 131. The screw head 20 and the fixator component 10 comprise a first material, and the lower tip portion 132 of the pin 30 comprises a material having a higher material hardness and compressive yield strength than the first material. The assembly 1 further comprises a wear resistant ceramic coating (not shown) over the screw head 20 and the fixator component 10.

Figure 10B:
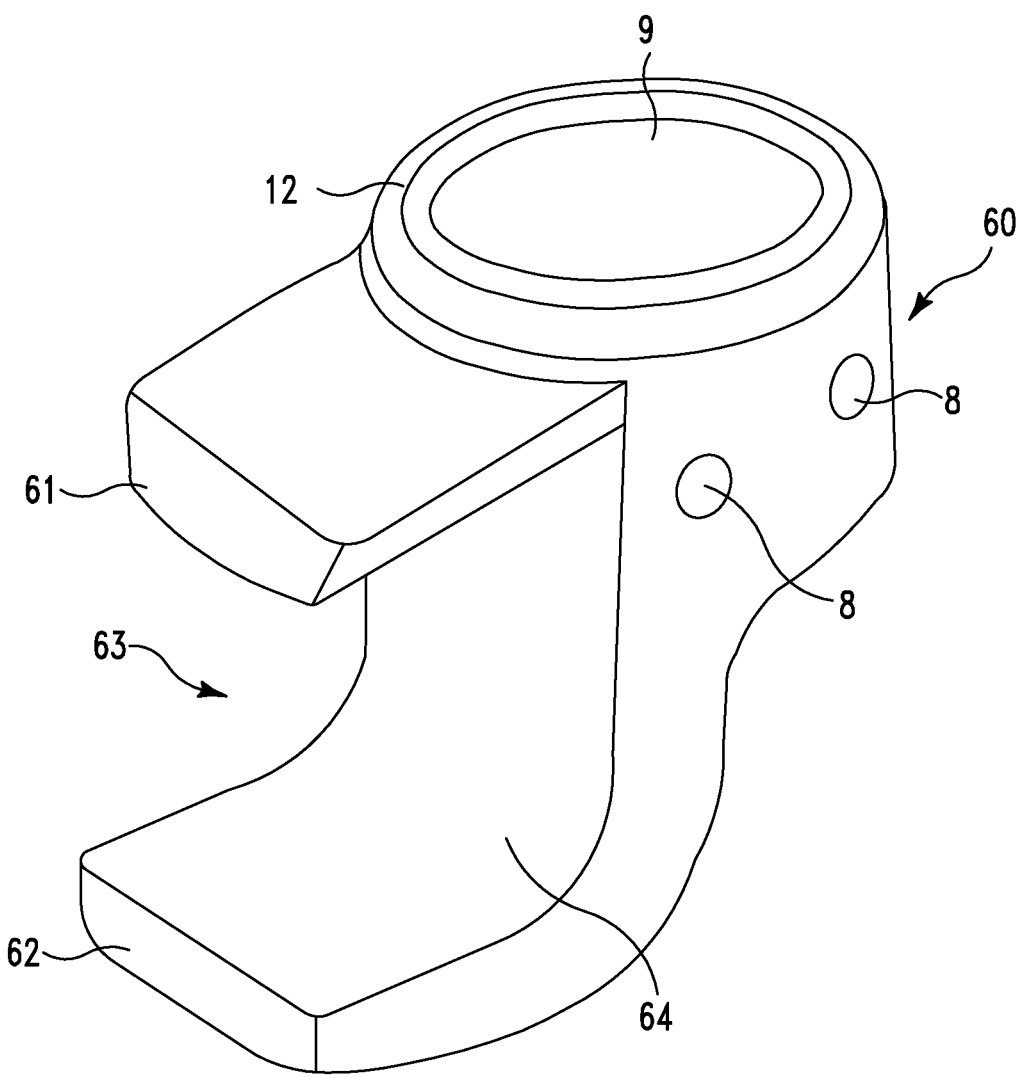
FIG. 10B is a detailed view of the hook of the bone fixator assembly of FIG. 10A according to the second embodiment herein.

The screw head 20 further comprises two opposed upright ends 22 separated by the slot 24, wherein each of the opposed upright ends 22 comprise an inner wall 27 and an outer wall 28, wherein the inner wall 27 comprises wall threads 23, and wherein the outer wall 28 comprises grooves (cuts) 29. The blocker 40 comprises blocker threads 41 configured around an outer perimeter 42 of the blocker 40, the blocker threads 41 being dimensioned and configured to mate with the wall threads 23. The upper saddle portion 131 of the pin 30 comprises a slot 32. The bulbous end 21 of the screw head 20 comprises a plurality of slots 6 terminating at an opening 4 at a tip 3 of the bulbous end 21. Moreover, the bulbous end 21 of the screw head 20 comprises a gap 19 configured to receive the pin 30. The concave socket 12 of the fixator component 10 comprises an inner portion 9 adapted to receive the bulbous end 21 of the screw head 20; and a dimpled outer portion 8. The fixator component 10 is configured as any of a threaded bone screw 10 (as shown in FIGS. 1 through 8) and a hook 60 (as shown in FIGS. 10A and 10B) according to the several embodiments herein.

The embodiments herein provide a pedicle screw assembly implant device 1, which may be used anteriorly or posteriorly, and which is capable of being utilized in surgeries to achieve anterior lumbar interbody fusion, posterior lumbar interbody fusion, transverse lumbar interbody fusion, correct degenerative disc disease, adult and pediatric scoliosis as a fixation device, and posterior cervical fusion.

Moreover, the embodiments herein provide a polyaxial spinal screw assembly 1 that can become rigid similar to a monoaxial screw inter-operatively on demand. The embodiments herein also offer the surgeon more lateral range of motion than conventional products by utilizing the space under the screw head 20 to provide a bigger arc of rotation. Moreover, the saddle pin 30 component offers the flexibility to use a diametrical range of spinal longitudinal members 50 instead of a fixed size longitudinal member.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A method comprising:
attaching a screw head to a bone fixator component, wherein said screw head comprises a first portion comprising a slot and an inwardly curved bottom portion; and a second portion comprising an outwardly protruding and expandable bulbous end extending from said inwardly curved bottom portion; and wherein said bone fixator component comprises a concave socket adapted to receive said screw head;
securing said bone fixator component in a bone;
securing a locking pin through said screw head causing said bulbous end to expand and lock into said concave socket of said bone fixator component;
inserting a longitudinal member in said screw head; and
inserting a blocker in said screw head.

2. The method of claim 1, further comprising coating said screw head and said bone fixator component with a wear resistant ceramic coating.

3. The method of claim 1, further comprising configuring said bone fixator component as a bone screw.

4. The method of claim 1, further comprising configuring said bone fixator component as a hook.

5. A method of assembling a pedicle fixation assembly, wherein said method comprises:
attaching a screw head to a bone fixator component, wherein said screw head comprises a bulbous end outwardly protruding from a bottom of said screw head;
securing said bone fixator component in a bone, wherein said bone fixator component comprises a concave socket;
securing a locking pin through said screw head causing said bulbous end to expand and lock into said concave socket of said bone fixator component;
inserting a longitudinal member in said screw head; and
inserting a blocker in said screw head.

6. The method of claim 5, further comprising coating said screw head and said bone fixator component with a wear resistant ceramic coating.

7. The method of claim 5, further comprising configuring said bone fixator component as a bone screw.

8. The method of claim 5, further comprising configuring said bone fixator component as a hook.

9. A method of using a pedicle screw assembly, said method comprising:
providing a screw head comprising:
a first portion comprising a slot and a curved bottom portion; and
a second portion comprising an outwardly protruding and expandable bulbous end extending from said curved bottom portion;
providing a bone fixator component comprising a concave socket that receives said screw head, wherein said bone fixator component is located completely outside of said screw head;
providing a locking pin that is adapted to be inserted through said screw head causing expansion of said expandable bulbous end of said screw head; and
providing a blocker that is adapted to engage said screw head.

10. The method of claim 9, further comprising providing said screw head and said bone fixator component with a wear resistant ceramic coating.

11. The method of claim 9, further comprising configuring said bone fixator component as a bone screw.

12. The method of claim 9, further comprising configuring said bone fixator component as a hook.

13. A method comprising:
providing a screw head comprising a slot and a bottom portion;
providing a polyaxial rotatable connecting end operatively connected to said bottom portion of said screw head;
providing a bone fixator component comprising a concave socket that receives said polyaxial rotatable connecting end;
configuring said rotatable connecting end to engage said bone fixator component;
inserting a longitudinal member in said slot; and
providing a blocker that engages said screw head and said longitudinal member, wherein said blocker causes said longitudinal member to lock said polyaxial rotatable connecting end in said concave socket.

14. The method of claim 13, wherein a combination of said bottom portion of said screw head with said polyaxial rotatable connecting end form a substantially bulbous body.

15. The method of claim 13, wherein said bone fixator component is located completely outside of said screw head.

16. The method of claim 13, wherein said bottom portion of said screw head and said polyaxial rotatable connecting end are adapted to be locked into said concave socket of said bone fixator component.

17. The method of claim 13, further comprising providing said screw head and said bone fixator component with a wear resistant ceramic coating.

18. The method of claim 13, further comprising configuring said bone fixator component as a bone screw.

19. The method of claim 13, further comprising configuring said bone fixator component as a hook.

* * * * *